United States Patent [19]
Kwak et al.

[11] Patent Number: 5,861,276
[45] Date of Patent: Jan. 19, 1999

[54] CDNAS ENCODING MURINE ANTIBODY AGAINST HUMAN PLASMA APOLIPOPROTEIN B-100

[75] Inventors: Ju-Won Kwak, Aeun-Dong; Moon-Hi Han, Yongjun-Dong; Byung-Kwon Choi, Kuam-Dong, all of Rep. of Korea

[73] Assignee: Korea Institute of Science & Technology, Rep. of Korea

[21] Appl. No.: 634,783

[22] Filed: Apr. 19, 1996

[30] Foreign Application Priority Data

Nov. 2, 1995 [KR] Rep. of Korea .................. 1995 39459

[51] Int. Cl.[6] .............................. C12P 21/06; C12N 1/21; C12N 15/13; C12N 15/70
[52] U.S. Cl. .................. 435/69.1; 435/71.1; 435/252.33; 435/320.1; 530/388.2; 530/388.25
[58] Field of Search ........................... 530/388.2, 388.25; 435/69.1, 71.1, 252.33, 320.1

[56] References Cited

PUBLICATIONS

Kwak, J–W. et al. Gene 169 (2): 237–239, Mar. 1996.
Reidl, L. S. et al. J. Immunol. 149: 471–480 Jul. 1992.
Pease, R. et al. J. Biol. Chem. 265: 553–568, Jan. 1990.
Winter, G. et al. Tips 14: 139–143, May 1993.
Bachorik et al., "Apolipoprotein measurements in clinical biochemistry and their utility vis–a–vis conventional assays" Clinica Chimica Acta 178, 1988, pp. 1–34.
Avogaro et al. "Are Apolipoproteins Better Discriminators Than Lipids For Atherosclerosis?", The Lancet, Apr. 28, 1979, pp. 901–903.
Riesen et al., "Apoproteins and Lipids as Discriminators of Severity of Coronary Heart Disease" Atherosclerosis, 37, 1980, pp. 157–162.
De Backer et al., "Discriminative Value of Lipids and Apoproteins in Coronary Heart Disease" Atherosclerosis, 42, 1982, pp. 197–203.
Herbert K. Naito, PhD., "The Clinical Significance of Apolipoprotein Measurements", J. of Clinical Immunoassay, vol. 9, No. 1, Spring, 1986, pp. 11–20.
Albers, et al., "Apoprotein Measurements and Their Clinical Application", Clinics in Laboratory Medicine, vol. 9, No. 1, Mar. 1989, pp. 137–192.
R. Rapley, "The Biotechnology and Applications of Antibody Engineering", Molecular Biotechnology, 3, May 1995, pp. 139–154.

*Primary Examiner*—Frank C. Eisenschenk
*Assistant Examiner*—Evelyn Rabin
*Attorney, Agent, or Firm*—Dilworth & Barrese

[57] ABSTRACT

The present invention relates to cDNAs encoding murine antibodies against apolipoprotein B-100. In addition, the present invention relates to methods of preparation of recombinant antibodies specific for human plasma apolipoprotein B-100 of LDL, and use thereof, for diagnosis and treatment of cardiovascular diseases.

6 Claims, 8 Drawing Sheets

```
  1 GAG GTG CAG CTG GTG GAG TCT GGA GCT GAG CTG ATG AAG CCT
    Glu Val Gln Leu Val Glu Ser Gly Ala Glu Leu Met Lys Pro ( 14)
                                            ---
 43 GGG GCC TCA GTG AAG ATA TCC TGC AAG GCT ACT GGC TAC ACA
    Gly Ala Ser Val Lys Ile Ser Cys Lys Ala Thr Gly Tyr Thr ( 28)
                                            ---
 85 TTC AGT AGC TAC TGG ATA GAG TGG ATA AAG CAG AGG CCT GGA
    Phe Ser Ser Tyr Trp Ile Glu Trp Ile Lys Gln Arg Pro Gly ( 42)
            CDR1
127 CAT GGC CTT GAG TGG ACT GGA GAG ATT TTA CCT GGA AGT GGT
    His Gly Leu Glu Trp Thr Gly Glu Ile Leu Pro Gly Ser Gly ( 56)
                            ---
169 ACT ACT AAA TAC AAT GAG AAG TTC AAG GAC AAG GCC ACA TTC
    Thr Thr Lys Tyr Asn Glu Lys Phe Lys Asp Lys Ala Thr Phe ( 70)
            CDR2                                    ---
211 ACT GCA GAT ACA TCC TCC AAC ACA GCC TAC ATG CAA CTC AGC
    Thr Ala Asp Thr Ser Ser Asn Thr Ala Tyr Met Gln Leu Ser ( 84)
253 AGC CTG ACA TCT GAG GAC TCT GCC GTC TAT TAC TGT GCA AGA
    Ser Leu Thr Ser Glu Asp Ser Ala Val Tyr Tyr Cys Ala Arg ( 98)
295 TCG TAT AGG TAC GCC CCT ATG GAC TAC TGG GGT CAA GGA ACC
    Ser Tyr Arg Tyr Ala Pro Met Asp Tyr Trp Gly Gln Gly Thr (112)
            CDR3
337 TCA GTC ACC GTC TCC TCA GCC AAA ACA ACA CCC CCA TCA GTC
    Ser Val Thr Val Ser Ser Ala Lys Thr Thr Pro Pro Ser Val (126)
                            CH1--->
379 TAT CCA CTG GCC CCT GGG TGT GGA GAT ACA ACT GGT TCC TCC
    Tyr Pro Leu Ala Pro Gly Cys Gly Asp Thr Thr Gly Ser Ser (140)
421 GTG ACT CTG GGA TGC CTG GTC AAG GGC TAC TTC CCT GAG TCA
    Val Thr Leu Gly Cys Leu Val Lys Gly Tyr Phe Pro Glu Ser (154)
463 GTG ACT GTG ACT TGG AAC TCT GGA TCC CTG TCC AGC AGT GTG
    Val Thr Val Thr Trp Asn Ser Gly Ser Leu Ser Ser Ser Val (168)
505 CAC ACC TTC CCA GCT CTC CTG CAG TCT GGA CTC TAC ACT ATG
    His Thr Phe Pro Ala Leu Leu Gln Ser Gly Leu Tyr Thr Met (182)
547 AGC AGC TCA GTG ACT GTC CCC TCC AGC ACC TGG CCA AGT CAG
    Ser Ser Ser Val Thr Val Pro Ser Ser Thr Trp Pro Ser Gln (196)
589 ACC GTC ACC TGC AGC GTT GCT CAC CCA GCC AGC AGC ACC ACG
    Thr Val Thr Cys Ser Val Ala His Pro Ala Ser Ser Thr Thr (210)
631 GTG GAC AAA AAA CTT GAG CCC AGC GGG CCC ATT TCA ACA ATC
    Val Asp Lys Lys Leu Glu Pro Ser Gly Pro Ile Ser Thr Ile (224)
673 AAC CCC TGT CCT CCA TGC  690
    Asn Pro Cys Pro Pro Cys (230)
```

Fig. 6

```
  1 GAT ATC AAG ATG ACC CAG TCT CCA TCT TCC ATG TAT GCA TCT
    Asp Ile Lys Met Thr Gln Ser Pro Ser Ser Met Tyr Ala Ser  ( 14)

43 CTA GGA GAG AGA GTC ACT ATC ACT TGC AAG GCG AGT CAG GAC
    Leu Gly Glu Arg Val Thr Ile Thr Cys Lys Ala Ser Gln Asp  ( 28)
                                        CDR1
 85 ATT TAT AGC TAT TTA AGC TGG TTC CAG CAG AAA CCA GGG AAA
    Ile Tyr Ser Tyr Leu Ser Trp Phe Gln Gln Lys Pro Gly Lys  ( 42)

127 TCT CCT AAG ACC CTG ATC TAT CGT GCA AAC AGA TTG GTC GAT
    Ser Pro Lys Thr Leu Ile Tyr Arg Ala Asn Arg Leu Val Asp  ( 56)
                                CDR2
169 GGG GTC CCA TCA AGG TTC AGT GGC AGT GGA TCT GGG CAA GAT
    Gly Val Pro Ser Arg Phe Ser Gly Ser Gly Ser Gly Gln Asp  ( 70)

211 TAT TCT CTC ACC ATC AGC AGC CTG GAG TAT GAA GAT CTG GGA
    Tyr Ser Leu Thr Ile Ser Ser Leu Glu Tyr Glu Asp Leu Gly  ( 84)

253 ATT TAT TAT TGT CTA CAG TTT GAT GAG TTT CCG TAC ACG TTC
    Ile Tyr Tyr Cys Leu Gln Phe Asp Glu Phe Pro Tyr Thr Phe  ( 98)
                    CDR3
295 GGA GGG GGG ACC AAG CTG GAA ATA AAA CGG GCT GAT GCT GCA
    Gly Gly Gly Thr Lys Leu Glu Ile Lys Arg Ala Asp Ala Ala  (112)
                                      CK--->
337 CCA ACT GTA TCC ATC TTC CCA CCA TCC AGT GAG CAG TTA ACA
    Pro Thr Val Ser Ile Phe Pro Pro Ser Ser Glu Gln Leu Thr  (126)

379 TCT GGA GGT GCC TCA GTC GTG TGC TTC TTG AAC AAC TTC TAC
    Ser Gly Gly Ala Ser Val Val Cys Phe Leu Asn Asn Phe Tyr  (140)

421 CCC AAA GAC ATC AAT GTC AAG TGG AAG ATT GAT GGC AGT GAA
    Pro Lys Asp Ile Asn Val Lys Trp Lys Ile Asp Gly Ser Glu  (154)

463 CGA CAA AAT GGC GTC CTG AAC AGT TGG ACT GAT CAG GAC AGC
    Arg Gln Asn Gly Val Leu Asn Ser Trp Thr Asp Gln Asp Ser  (168)

505 AAA GAC AGC ACC TAC AGC ATG AGC AGC ACC CTC ACG TTG ACC
    Lys Asp Ser Thr Tyr Ser Met Ser Ser Thr Leu Thr Leu Thr  (182)

547 AAG GAC GAG TAT GAA CGA CAT AAC AGC TAT ACC TGT GAG GCC
    Lys Asp Glu Tyr Glu Arg His Asn Ser Tyr Thr Cys Glu Ala  (196)

589 ACT CAC AAG ACA TCA ACT TCA CCC ATT GTC AAG AGC TTC AAC
    Thr His Lys Thr Ser Thr Ser Pro Ile Val Lys Ser Phe Asn  (210)

631 AGG AAT GAG TGT   642
    Arg Asn Glu Cys  (214)
```

Fig. 7

```
  1 GAG GTG CAG CTG GTG GAG TCA GGA CCT GGC CTG GTG GCG CCC
    Glu Val Gln Leu Val Glu Ser Gly Pro Gly Leu Val Ala Pro ( 14)
    ---             ---
 43 TCA CAG AGC CTG TCC ATC ACG TGC ACT GTC TCA GGG TTC TCA
    Ser Gln Ser Leu Ser Ile Thr Cys Thr Val Ser Gly Phe Ser ( 28)

85 TTA ACC GAC TAT GGT GTA AGC TGG ATT CGC CAG CCT CCA GGA
    Leu Thr Asp Tyr Gly Val Ser Trp Ile Arg Gln Pro Pro Gly ( 42)
            CDR1
127 AAG GGT CTG GAG TGG CTG GGA GTA ATT TGG GCT GGT GGA AGC
    Lys Gly Leu Glu Trp Leu Gly Val Ile Trp Ala Gly Gly Ser ( 56)
                                CDR2
169 ACA TTC TAT AAT TCA GCT CTC AAG TCC AGA CTG AGC ATC AAC
    Thr Phe Tyr Asn Ser Ala Leu Lys Ser Arg Leu Ser Ile Asn ( 70)

211 AAG GAC AAC TCC AAG AGC CAA GTT TTC TTA AAA ATG AAC AGT
    Lys Asp Asn Ser Lys Ser Gln Val Phe Leu Lys Met Asn Ser ( 84)

253 CTG CAC ACT GAT GAC ACA GCC ATG TAC TAC TGT GTC AAA CAT
    Leu His Thr Asp Asp Thr Ala Met Tyr Tyr Cys Val Lys His ( 98)
                                                        ---
295 GAG GAT AGG TAC GAC TGG TAC TTC GAT GTC TGG GGC GCA GGG
    Glu Asp Arg Tyr Asp Trp Tyr Phe Asp Val Trp Gly Ala Gly (112)
            CDR3
337 ACC ACG GTC ACC GTC TCC TCA GCC AAA ACA ACA CCC CCA TCA
    Thr Thr Val Thr Val Ser Ser Ala Lys Thr Thr Pro Pro Ser (126)
                                C_H1--->
379 GTC TAT CCA CTG GCC CCT AGG TGT GGA GAT ACA ACT GGT TCC
    Val Tyr Pro Leu Ala Pro Arg Cys Gly Asp Thr Thr Gly Ser (140)
                            ---
421 TCC GTG ACT CTG GGA TGC CTG GTC AAG GGC TAC TTC CCT GAG
    Ser Val Thr Leu Gly Cys Leu Val Lys Gly Tyr Phe Pro Glu (154)

463 TCA GTG ACT GTG ACT TGG AAC TCT GGA TCC CTG TCC AGC AGT
    Ser Val Thr Val Thr Trp Asn Ser Gly Ser Leu Ser Ser Ser (168)

505 GTG CAC ACC TTC CCA GCT CTC CTG CAG TCT GGA CTC TAC ACT
    Val His Thr Phe Pro Ala Leu Leu Gln Ser Gly Leu Tyr Thr (182)

547 ATG AGC AGC TCA GTG ACT GTC CCC TCC AGC ACC TGG CCA AGT
    Met Ser Ser Ser Val Thr Val Pro Ser Ser Thr Trp Pro Ser (196)

589 CAG ACC GTC ACC TGC AGC GTT GCT CAC CCA GCC AGC AGC ACC
    Gln Thr Val Thr Cys Ser Val Ala His Pro Ala Ser Ser Thr (210)

631 ACG GTG GAC AAA AAA CTT GAG CCC AGC GGG CCC ATT TCA ACA
    Thr Val Asp Lys Lys Leu Glu Pro Ser Gly Pro Ile Ser Thr (224)

673 ATC AAC CCC TGT CCT CCA TGC  693
    Ile Asn Pro Cys Pro Pro Cys (231)
```

Fig. 8

```
  1 CAG GCT GTT GTG ACT CAG GAA TCT GCA CTC ACC ACA TCA CCT
    Gln Ala Val Val Thr Gln Glu Ser Ala Leu Thr Thr Ser Pro  ( 14)

43 GGT GAA ACA GTC ACA CTC ACT TGT CGC TCA AAT ACT GGG GCA
    Gly Glu Thr Val Thr Leu Thr Cys Arg Ser Asn Thr Gly Ala  ( 28)
                                    ─────────────────────
                                             CDR1
 85 GTT ACA ACT AGT AAC TAT GCC AGC TGG GTC CAA GAA AAA CCA
    Val Thr Thr Ser Asn Tyr Ala Ser Trp Val Gln Glu Lys Pro  ( 42)
    ───────────────────────────────

127 GAT CAT TTA TTC ACT GGT CTA ATA GGT GGT ACC AAC AAC CGA
    Asp His Leu Phe Thr Gly Leu Ile Gly Gly Thr Asn Asn Arg  ( 56)
                                        ─────────────────
                                                CDR2
169 GTT CCA GGT GTT CCT GCC AGG TTC TCA GGC TCC CTG ATT GGA
    Val Pro Gly Val Pro Ala Arg Phe Ser Gly Ser Leu Ile Gly  ( 70)
    ───────

211 GAC AAG GCT GCC CTC ACC ATC ACA GGG GCA CAG ACT GAG GAT
    Asp Lys Ala Ala Leu Thr Ile Thr Gly Ala Gln Thr Glu Asp  ( 84)

253 GAG GCA ATA TAT TTC TGT GCT CTA TGG AAC AGC AAC CAC TGG
    Glu Ala Ile Tyr Phe Cys Ala Leu Trp Asn Ser Asn His Trp  ( 98)
                            ─────────────────────────────
                                         CDR3
295 GTG TTC GGT GGA GGA ACC AAA CTG ACT GTC CTA GGC CAG CCC
    Val Phe Gly Gly Gly Thr Lys Leu Thr Val Leu Gly Gln Pro  (112)
    ───                                             ───────
                                                     Cλ --->
337 AAG TCT TCG CCA TCA GTC ACC CTG TTT CCA CCT TCC TCT GAA
    Lys Ser Ser Pro Ser Val Thr Leu Phe Pro Pro Ser Ser Glu  (126)

379 GAG CTC GAG ACT AAC AAG GCC ACA CTG GTG TGT ACG ATC ACT
    Glu Leu Glu Thr Asn Lys Ala Thr Leu Val Cys Thr Ile Thr  (140)

421 GAT TTC TAC CCA GGT GTG GTG ACA GTG GAC TGG AAG GTA GAT
    Asp Phe Tyr Pro Gly Val Val Thr Val Asp Trp Lys Val Asp  (154)

463 GGT ACC CCT GTC ACT CAG GGT ATG GAG ACA ACC CAG CCT TCC
    Gly Thr Pro Val Thr Gln Gly Met Glu Thr Thr Gln Pro Ser  (168)

505 AAA CAG AGC AAC AAC AAG TAC ATG GCT AGC AGC TAC CTG ACC
    Lys Gln Ser Asn Asn Lys Tyr Met Ala Ser Ser Tyr Leu Thr  (182)

547 CTG ACA GCA AGA GCA TGG GAA AGG CAT AGC AGT TAC AGC TGC
    Leu Thr Ala Arg Ala Trp Glu Arg His Ser Ser Tyr Ser Cys  (196)

589 CAG GTC ACT CAT GAA GGT CAC ACT GTG GAG AAG AGT CTG TCT
    Gln Val Thr His Glu Gly His Thr Val Glu Lys Ser Leu Ser  (210)

631 CGT GCT GAC TGT   642
    Arg Ala Asp Cys  (214)
```

CDNAS ENCODING MURINE ANTIBODY AGAINST HUMAN PLASMA APOLIPOPROTEIN B-100

TECHNICAL FIELD

The present invention relates to cDNAs encoding murine monoclonal antibody against apolipoprotein B-100, the protein of low-density lipoproteins(LDL) in human plasma.

More specifically, the present invention relates to cDNAs encoding heavy chain and light chain of murine monoclonal antibody which recognizes and binds to apolipoprotein B-100. Apolipoprotein B-100 is the major protein moiety of LDL which plays an important role in the plasma lipid metabolism, transporting cholesterol from liver to necessary peripheral tissue.

BACKGROUND OF ART

Apolipoprotein B-100, the protein of low density lipoproteins in human plasma, is reported to be a more reliable positive index than former cholesterol index of LDL-cholesterol, for diagnosis of cardiovascular diseases, such as arteriosclerosis, coronary artery disease, and the like [Brustolin, D. et al., Clin. Chem. 37: 742–747 (1991); Dona, V. et al., Giorn. It. Chim. Clin. 12: 205–214 (1987)].

The specific monoclonal antibody can be used as a diagnostic agent to measure the concentration of apolipoprotein B-100 in blood conveniently and reliably for the global risk estimation of cardiovascular diseases. In addition the specific monoclonal antibody against apolipoprotein B-100 can be used for specific binding and removal of the high level of blood LDL for the treatment of cardiovascular diseases. Therefore, it is necessary to produce specific monoclonal antibodies against apolipoprotein B-100.

SUMMARY OF THE INVENTION

The object of the present invention is to provide cloned cDNAs, which encode antigen-binding fragment(Fab) of murine monoclonal antibodies binding specifically with human plasma apolipoprotein B-100. These monoclonal antibodies are MabB9 with IgG2b heavy chain and kappa light chain, and MabB23 with IgG2b heavy chain and lambda light chain. The hybridoma cells producing MabB9 and MabB23, H-MabB9 and H-MabB23, respectively, have been deposited with GERI, KIST as accession numbers KCTC 0104 BP (H-MabB9) and KCTC 0105 BP (H-MabB23) on Mar. 23, 1994 [Reference Patent Application #94-12084, Republic of Korea, May 31, 1994]

The object of the present invention is to provide cDNAs of heavy chain gene(B9H) and light chain gene(B9L), which encode antigen-binding fragment (Fab) of murine monoclonal antibody, MabB9, and to provide cDNAs of heavy chain gene(B23H) and light chain gene(B23L), which encode the Fab fragment of murine monoclonal antibody, MabB23.

And the object of the present invention is to provide *Escherichia coli* transformant, TG1/pB9HT7, containing the vector pB9HT7, in which the heavy chain gene, B9H, is inserted(depositary authority: Genetic Engineering Research Institute, KIST, Korea; accession number: KCTC 0197 BP; accession date: Oct. 6, 1995) and *E. coli* transformant, TG1/pB9LBlue, containing the vector pB9LBlue, in which the light chain gene, B23H, is inserted (depositary authority: Genetic Engineering Research Institute, KIST, Korea; accession number: KCTC 0198 BP; accession date: Oct. 6, 1995).

And the object of the present invention is to provide *E. coli* transformant, TG1/pB23HT7, containing the vector pB23HT7, in which the heavy chain gene, B23H, is inserted (depositary authority: Genetic Engineering Research Institute, KIST, Korea; accession number: KCTC 0199 BP; accession date: Oct. 6, 1995) and *E. coli* transformant, TG1/pB23LBlue, containing the vector pB23LBlue, in which the former light chain gene, B23L, is inserted (depositary authority: Genetic Engineering Research Institute, KIST, Korea; accession number: KCTC 0199 BP; accession date: Oct. 6, 1995).

In addition, the object of the present invention is to provide the method of preparation of recombinant antibody against human plasma lipoprotein B-100 by expressing the cloned cDNAs via the construction of an expression vector for appropriate host cells such as *E. coli*.

In addition, the object of the present invention is to provide the use of recombinant antibody against human plasma apolipoprotein B-100 for diagnosis of cardiovascular diseases by allowing measurement of the concentration of human plasma apolipoprotein B-100.

In addition, the object of the present invention is to provide the use of recombinant antibody against human plasma apolipoprotein B-100 for treatment of cardiovascular diseases by allowing the specific binding and removal of the high level LDL or other apolipoprotein B-100 containing harmful substances from blood.

In the following, the present invention will be described in detail.

BRIEF DESCRIPTION OF FIGURES

FIG. 5 shows nucleotide sequence SEQ ID No. 1 and deduced amino acid sequence of cDNA (B9H) encoding the heavy chain of murine monoclonal antibody, MabB9, against human plasma apolipoprotein B-100, prepared according to this invention. CDR 1, 2, 3 sequences within V-region and $C_H1$-region (from nucleotide No. 355) are underlined. Unusual amino acids found when compared with those of mouse heavy chain subgroup II(B) are indicated with dotted line under the very amino acid.

FIG. 6 shows nucleotide sequence SEQ ID No. 2 and deduced amino acid sequence of cDNA (B9L) encoding light chain of murine monoclonal antibody, MabB9, against human plasma apolipoprotein B-100, prepared according to this invention. CDR 1, 2, 3 sequences within V-region and $C_K1$-region (from nucleotide No. 322) are underlined.

FIG. 7 shows nucleotide sequence SEQ ID No. 3 and deduced amino acid sequence of cDNA (B23H) encoding the heavy chain of murine monoclonal antibody, MabB23, against human plasma apolipoprotein B-100, prepared according to this invention. CDR 1, 2, 3 sequences within V-region and $C_H1$-region (from nucleotide No. 358) are underlined. Unusual amino acids found when compared with those mouse heavy chain subgroup I(B) are indicated with dotted line under the very amino acid.

FIG. 8 shows nucleotide sequence SEQ ID No. 4 and deduced amino acid sequence of cDNA (B23L) encoding the light chain of murine monoclonal antibody, MabB23, against human plasma apolipoprotein B-100, prepared according to this invention. CDR 1, 2, 3 sequences within V-region and $C_\lambda 1$-region (from nucleotide No. 331) are underlined.

DETAILED DESCRIPTION OF THE PREFERRED EMBODIMENTS

Figure 1:
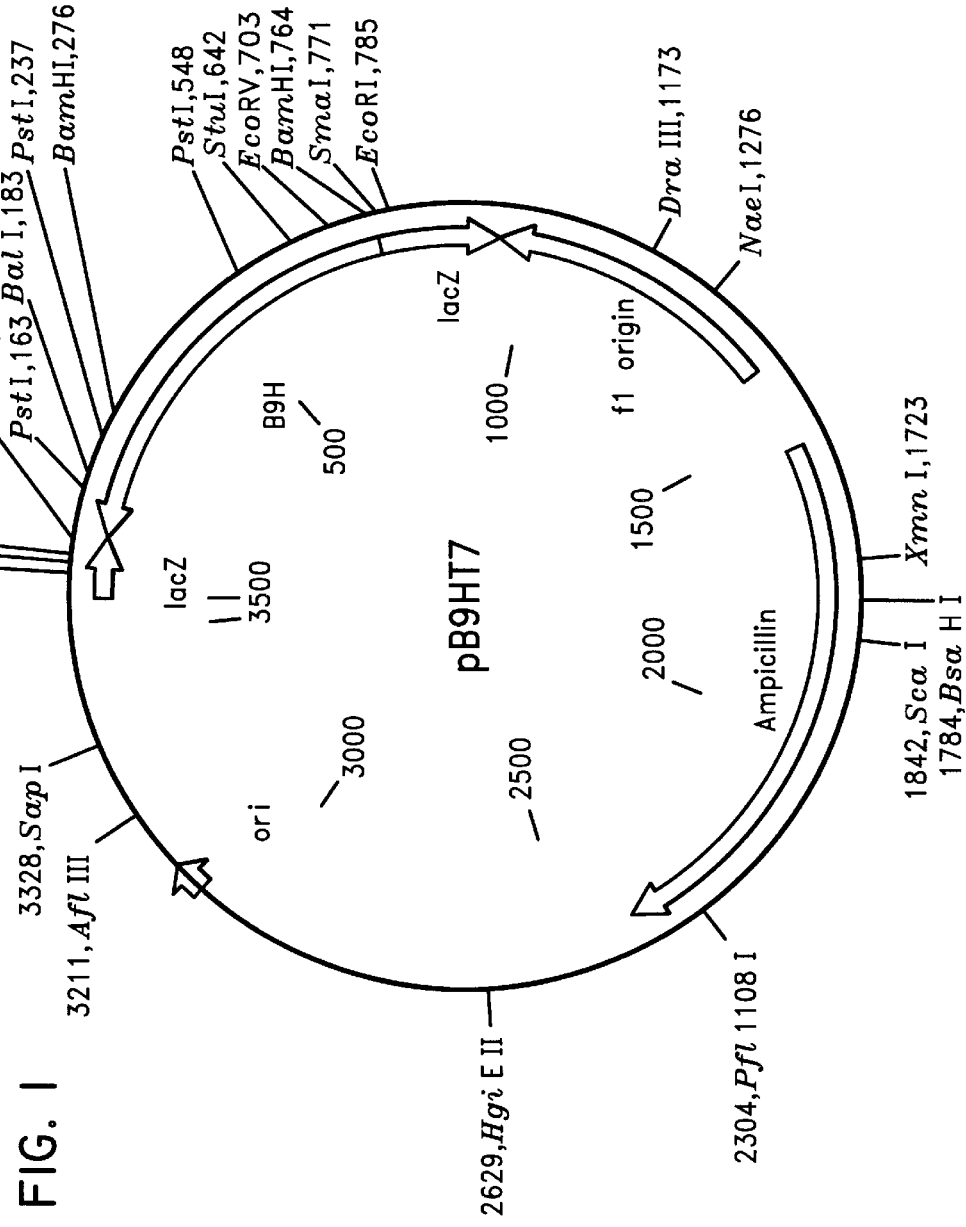
FIG. 1 shows the structure and restriction map of pB9HT7 vector containing 690 bp SEQ ID NO. 1 cDNA of the heavy chain (B9H) of murine monoclonal antibody, MabB9, against human plasma apolipoprotein B-100, prepared according to this invention.

Hybridoma cells producing murine monoclonal antibody against human plasma apolipoprotein B-100 are cultured with optimal media, such as RPMI medium, (Sigma, R-6504) and harvested. Then, the total RNAs of the cells are extracted by acid guanidium thiocyanate-phenol-chloroform method and the like. Also, the poly(A)$^+$ RNA is purified by oligo(dT)-cellulose chromatography method [Aviv, H. and Leder, P., Proc. Natl. Acad. Sci. USA, 69: 1408–1412, 1972].

Next, the first strand of cDNA is synthesized by using reverse transcriptase and oligo(dT)$_{15}$ primer. In order to get the cDNAs encoding heavy chain and light chain of antibody, polymerase chain reaction(PCR) is performed by Taq DNA polymerase using the specific oligonucleotide primers corresponding to N-terminal and C-terminal sequences of the heavy and light chains of antibody. The N-terminal primer used is synthesized according to the data obtained from N-terminal sequencing of the purified heavy and light chain proteins of the antibody, and the C-terminal primer used is obtained according to the constant region sequences of the heavy and light chains of the antibody.

The DNA fragments obtained by the polymerase chain reactions are cloned into proper vectors, such as pT7Blue (Novagen, USA) and pBluescript(Stratagene, USA). Nucleotide sequences of the cloned cDNAs are determined by chain termination method using dideoxy nucleotides and the like [Sanger, F. et al., Proc. Natl. Acad. Sci. USA, 76: 4350–4354, 1977].

The following examples will further illustrate the present invention, which by no means limit the present invention.

<Example 1> mRNA purification from hybridoma cells producing monoclonal antibodies against human plasma apolipoprotein B-100

The hybridoma cells, H-MabB9(depositary authority: GERI, KIST; accession number: KCTC 0104 BP; accession date: Mar. 23, 1994) producing monoclonal antibody MabB9 (IgG2b, kappa) against human plasma apolipoprotein B-100, and H-MabB23 (depositary authority: GERI, KIST; accession number: KCTC 0105 BP; accession date: Mar. 23, 1994) producing monoclonal antibody MabB23 (IgG2b, lambda) were made by the process, wherein pancreatic cells of Balb/c mouse and myeloma cell that has been previously immunized with human apolipoprotein B-100 were fused with the myeloma cells of Sp2/0-Ag-14 by the well-established hybridoma technique established well [Kohler, G. and Milstein, C., Nature, 256: 495–497, 1975; Galfre, G. et al., Nature, 256: 550–552, 1977]. These hybridoma cells were cultured in optimal media, such as RPMI medium (Sigma, R-6504), and harvested.

Then, the total cellular RNA was extracted by acid guanidium thiocyanate-phenol-chloroform method [Puissant, C. and Houdebine, L. M., Biotechnique, 8: 148–149, 1990].

And the poly (A)+RNA was purified by oligo(dT)-cellulose chromatography method [Aviv, H. and Leder, P., Proc. Natl. Acad. Sci. USA, 69: 1408–1412, 1972]

<Example 2>

N-terminal amino acid sequencing of heavy and in light chains of monoclonal antibody MabB9 against human plasma apolipoprotein B-100.

Murine monoclonal antibody MabB9 against human plasma apoliporotein B-100 was mixed with Laemmli's sample buffer [Laemmli, E. K., Nature, 227: 680–685, 1970], including mercaptoethanol. The antibody was separated by SDS-polyacrylamide gel electrophoresis and transferred onto PVDF membrane by electroblotting method [Towbin, H. et al., Proc. Natl. Acad. Sci. USA, 76: 4350–4354, 1979). Then, about 50-kD band corresponding to the heavy chain and 25-kD band corresponding to light chain of monoclonal antibody MabB9 were cut to analyze their N-terminal amino acid sequences by amino acid sequence analyzer.

As a result, the N-terminal amino acid sequence of the heavy chain of monoclonal antibody MabB9 was determined as E-V-Q-L-V-E-S-G-A-E SEQ ID No. 5 and that of the light chain of MabB9 was determined as D-I-K-M-T-Q-S-P-S-S SEQ ID No. 6.

<Example 3>

N-terminal amino acid sequencing of heavy and light chains of monoclonal antibody MabB23 against human plasma apolipoprotein B-100.

Murine monoclonal antibody MabB23 against human plasma apoliporotein B-100 was incubated with Laemmli's sample buffer. The antibody was separated by SDS-polyacrylamide gel electrophoresis and transferred onto PVDF membrane by electroblotting method. Then, about 50-kD band corresponding to the heavy chain and 25-kD band corresponding to light chain of monoclonal antibody MabB23 were cut to analyze their N-terminal amino acid sequences by amino acid sequence analyzer.

As a result, the N-terminal amino acid sequence in heavy chain of monoclonal antibody MabB23 was determined as E-V-Q-L-V-E-S-G-P-G SEQ ID N. 7 and that in light chain of monoclonal antibody MabB23 as Q-A-V-V-T-Q-E-S-A-L SEQ ID No. 8.

<Example 4 > cDNA cloning of heavy and light chains of murine monoclonal antibody MabB9 against human plasma apolipoprotein B-100.

To synthesize the first strand of cDNA, 1 μg of poly (A)$^+$ RNA of H-MabB9 Hybridoma cell purified in Example 1 was incubated with 1 mM each of 4 dNTPs, 50 units of RNasin (Boehringer Mannheim, USA), 80 pmoles of oligo d(T)$_{15}$ primer and 15 unit of AMV reverse transcriptase in 20 μℓ of the reaction buffer (50 mM KCl, 50 mM Tris-Cl (pH8.3), 10 mM MgCl$_2$, 1 mM spermidine, 10 mM DTT, 4 mM sodium pyrophosphate] at 42° C. for 1 hr. Then, N-terminal and C-terminal oligonucleotide primers and 2 units of Taq DNA polymerase were added to perform the polymerase chain reaction (PCR). The N-terminal oligonucleotide primers were synthesized according to the codons of N-terminal amino acid sequences determined in Example 2, and the C-terminal oligonucleotide primers were synthesized according to the constant region sequences of IgG2b heavy chain and kappa light chain of monoclonal antibody MabB9. The PCR was performed according to the steps, wherein the reaction mixture was incubated initially at 94° C. for 15 sec, at 57° C. for 10 sec and at 72° C. for 15 sec, and then at 94° C. for 5 sec, at 57° C. for 10 sec, at 72° C. for 15 sec sequentially and repeatedly for 33 cycles, and finally at 94° C. for 15 sec, at 57° C. for 10 sec and at 72° C. for 120 sec. As a result, 690 bp of DNA fragment corresponding to Fab region of the heavy chain of monoclonal antibody MabB9 was obtained. The DNA fragment was cloned into pT7Blue(Novagene, USA) phagemid vector to construct pB9HT7 containing B9H, the heavy chain cDNA of monoclonal antibody MabB9. The structure and restriction map of pB9HT7 is shown in FIG. 1.

Figure 2:
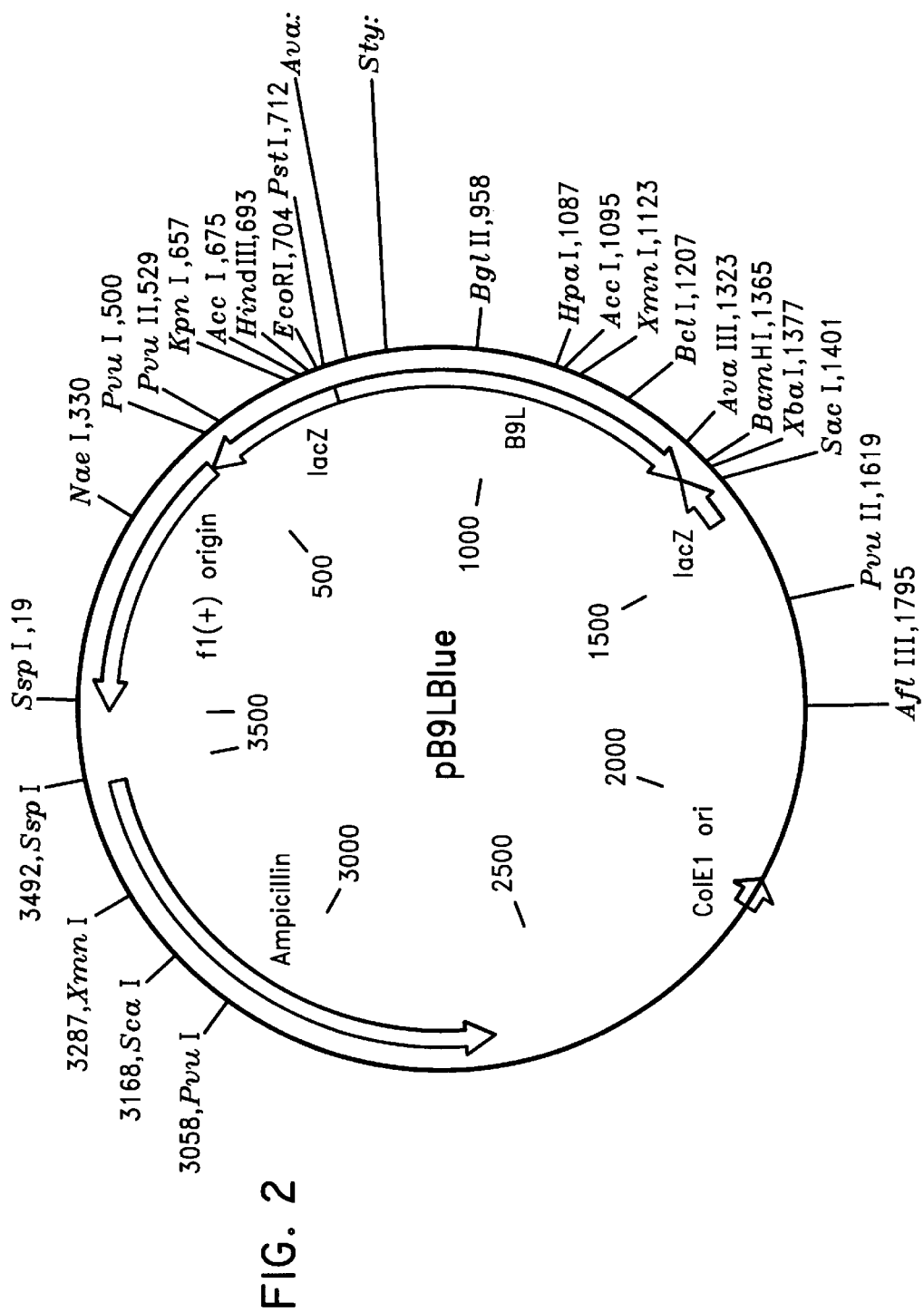
FIG. 2 shows the structure and restriction map of pB9LBlue vector containing 642 bp cDNA SEQ ID NO. 2 of the light chain (B9L) of murine monoclonal antibody, MabB9, against human plasma apolipoprotein B-100, prepared according to this invention.

Likewise, 642 bp DNA fragment corresponding to the light chain of monoclonal antibody MabB9 was obtained and cloned into pBluescript(Stratagene, USA) phagemid vector to construct pB9LBlue containing B9L, light chain cDNA of monoclonal antibody MabB9. The structure and restriction map of pB9LBlue is shown in FIG. 2.

With the above described vectors, *Escherichia coli* TG1 strains were transformed to obtain TG1/pB9HT7 and TG1/pB9LBlue. And the strains were deposited with GERI, KIST on Oct. 6, 1995(respective accession numbers: KCTC 0197 BP and KCTC 0198 BP).

<Example 5> cDNA cloning of heavy and light chains of murine monoclonal antibody MabB23 against human plasma apolipoprotein B-100

1 µg of poly(A)$^+$ RNA of H-MabB23 hybridoma cell purified in Example 1 was incubated with AMV reverse transcriptase, and the same method as described in Example 4 was performed to synthesize the first strand cDNA. Then, N-terminal oligonucleotide primers synthesized according to the N-terminal amino acid sequencing data obtained in Example 3 for the heavy and light chains of monoclonal antibody MabB23, and C-terminal oligonucleotide primers synthesized according to the constant region sequences of the IgG2b heavy chain and lambda light chain, were added to perform the PCR reactions using the same reaction conditions as described in Example 4.

Figure 3:
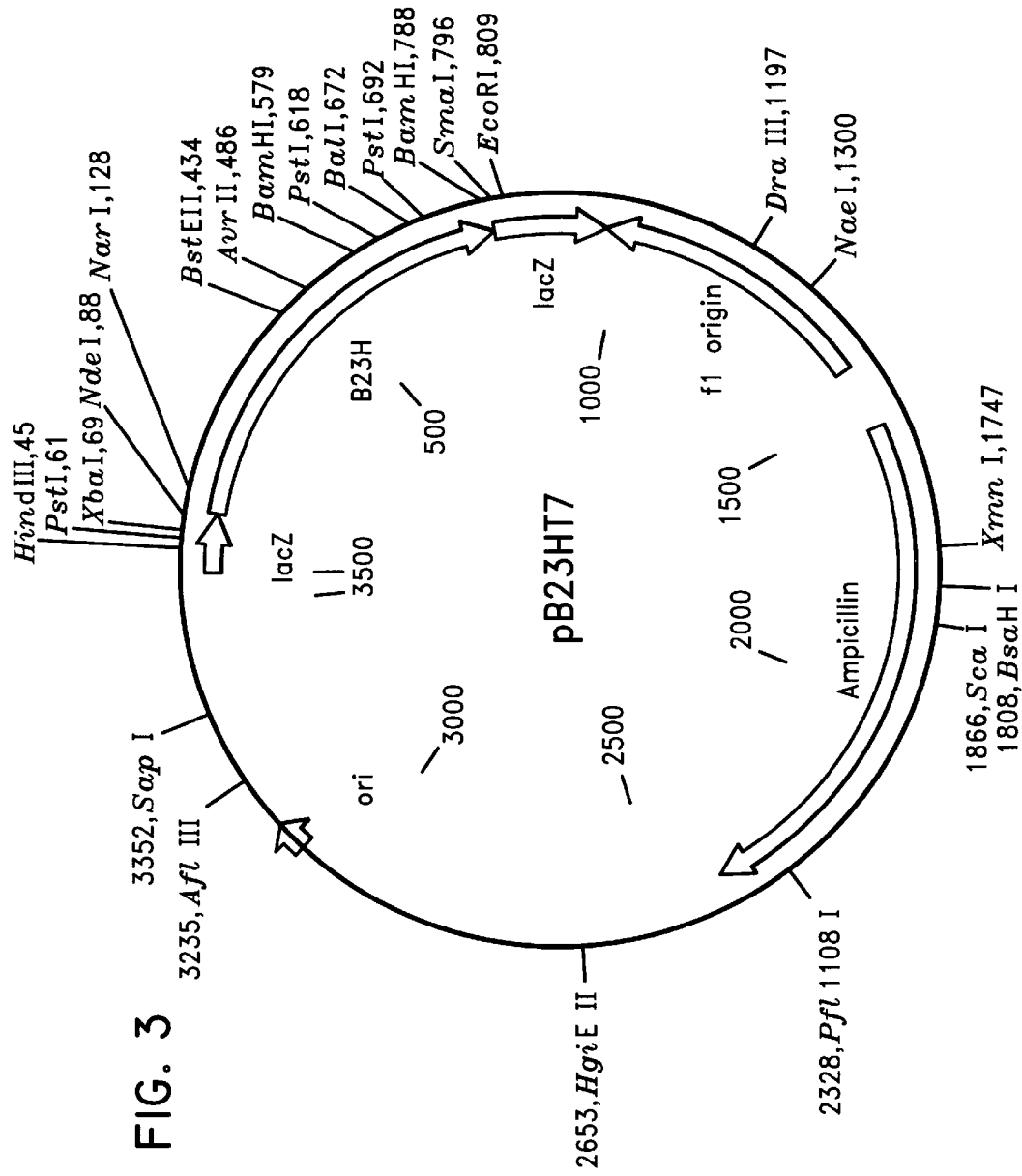
FIG. 3 shows the structure and restriction map of pB23HT7 vector containing 693 bp cDNA SEQ ID NO. 3 of the heavy chain (B23H) of murine monoclonal antibody, MabB23, against human plasma apolipoprotein B-100, prepared according to this invention.

As a result, 693 bp DNA fragment corresponding to Fab region of the heavy chain of monoclonal antibody MabB23 was obtained. The DNA fragment was cloned into pT7Blue vector to construct pB23HT7 containing B23H, the heavy chain cDNA of monoclonal antibody MabB23. The structure and restriction map of pB23HT7 is shown in FIG. 3.

Figure 4:
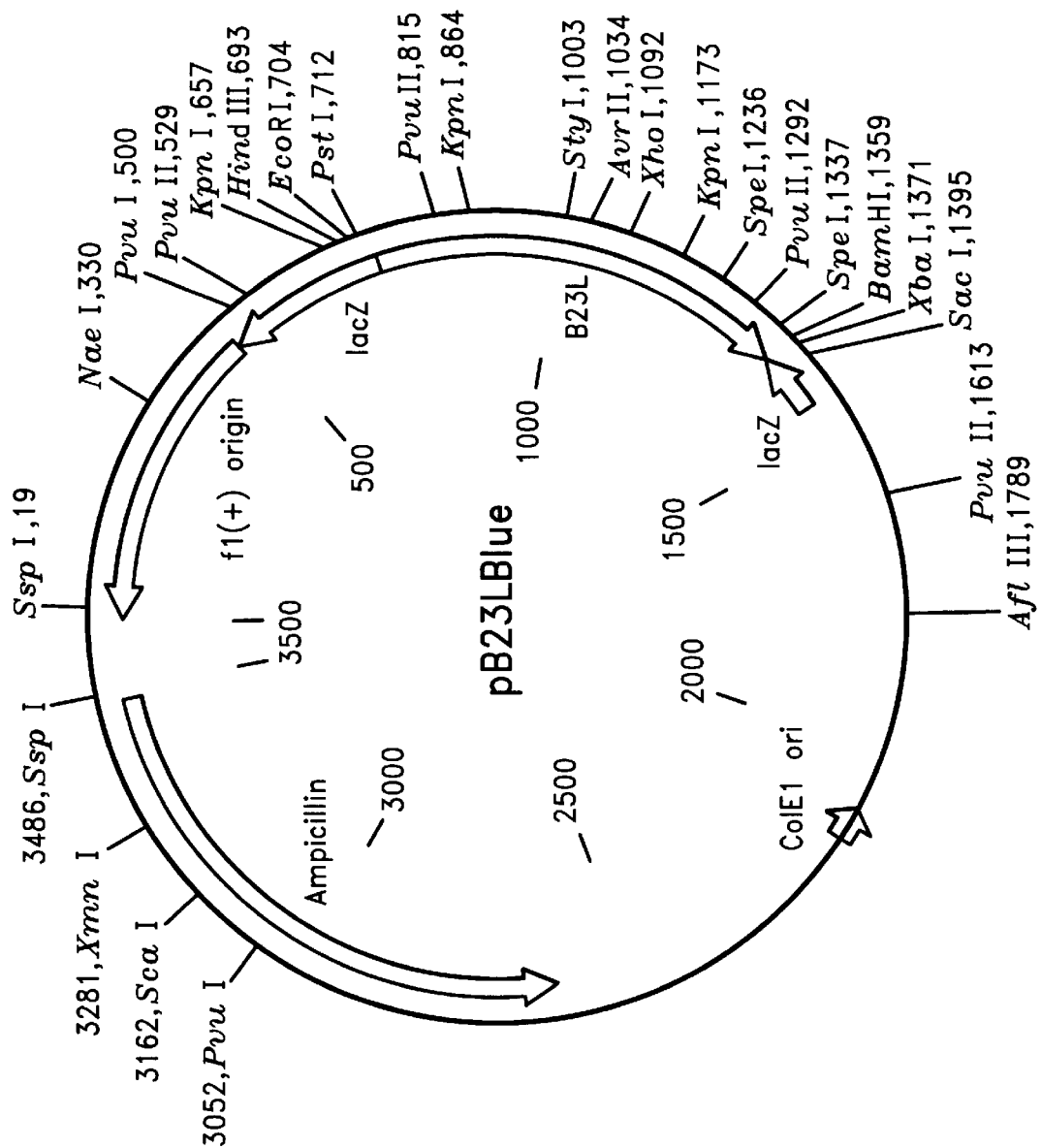
FIG. 4 shows the structure and restriction map of pB23LBlue vector containing 642 bp cDNA SEQ ID No. 4 of the light chain (B23L) of murine monoclonal antibody, MabB23, against human plasma apolipoprotein B-100, prepared according to this invention.

Likewise, 642 bp DNA fragment corresponding to the light chain of monoclonal antibody MabB23 was obtained, and cloned into pBluescript vector to construct pB23LBlue containing B23L, the light chain cDNA of monoclonal antibody MabB23. The structure and restriction map of pB23LBlue is shown in FIG. 4.

With the above-described vectors, *Escherichia coli* TG1 strain was transformed to obtain TG1/pB23HT7 and TG1/pB23LBlue. The strains were deposited with GERI, KIST on Oct. 6, 1995 (respective accession number : KCTC 0199 BP and KCTC 0200 BP)

<Example 6>

Nucleotide sequencing of heavy chain CDNA of murine monoclonal antibody MabB9 against human plasma apolipoprotein B-100

To determine the nucleotide sequence of the heavy chain cDNA of the murine monoclonal antibody MabB9 against human plasma apoliporotein B-100, double stranded or single stranded phagemid DNA of pB9HT7 which contains the heavy chain cDNA(B9H) cloned in Example 4 was purified by SDS-alkaline extraction method [Birnboim, H. C., Methods Enzymol., 100: 243–255, 1983]. Nucleotide sequence of the antibody CDNA was determined by chain termination method using dideoxy nucleotides [Sanger, F. et al., Proc. Natl. Acad. Sci. USA, 74: 5463–5467, 1977], wherein the nucleotide sequence was fully determined on both orientations using M13 universal primer or synthetic internal primers.

The determined nucleotide sequence of MabB9 heavy chain CDNA in MabB9 is shown in FIG. 5. When compared with the reported immunoglobulin heavy chain cDNA sequences, it was found that the heavy chain CDNA of MabB9, B9H, belongs to mouse heavy chain subgroup II(B)[Kabat, E. A. et al., Sequences of Proteins of Immunological Interest, 5th ed., US Department of Human Services, Public Health Service, National Institute of Health, Bethesda, Md., 1991]. The V(variable)-region was located between amino acid number(No.) 1 and No. 118 and $C_H1$-region located from No. 119. And V-region also contained unique CDR(complementarity determining sequences) 1, 2, 3 sequences, located between amino acid No. 31 and No. 35 (CDR 1), between No. 50 and No. 66 (CDR 2) and between No. 99 and No. 107 (CDR 3), which confer antigen-binding specificity. 7 Cysteine residues were found at amino acid numbers 22, 96, 133, 145, 200, 227 and 230, which would participate in disulfide bonding to form Fab structure of antibody.

When compared with the V-region sequence profiles of mouse heavy chain subgroup II(B) [Harris, L. and Bajorath, J., Protein Sci. 4: 306–310, 1995], some unusual amino acids were found at the following locations: Met (No. 13), Thr (No. 25), Thr(No. 48) and Phe (No. 70) .

<Example 7>

Nucleotide sequencing of light chain CDNA of murine monoclonal antibody MabB9 against human plasma apoliprotein B-100.

To determine the nucleotide sequence of the light chain CDNA of the murine monoclonal antibody MabB9 against human plasma apoliporotein B-100, double stranded or single stranded phagemid DNA of pB9LBlue which contains the light chain cDNA (B9L) cloned in Example 4 was purified by the SDS-alkaline extration method [Birnboim, H. C., 1983]. Nucleotide sequence of the antibody cDNA was determined by the chain termination method using dideoxy nucleotides [Sanger, F. et al., 1977], wherein the nucleotide sequence was fully determined on both orientations using M13 universal primer or synthetic internal primers.

The nucleotide sequence of MabB9 light chain cDNA is shown in FIG. 6. When compared with the reported immunoglobulin light chain cDNA sequences, it was found that the light chain cDNA of MabB9, B9L, belongs to mouse kappa chain subgroup V [Kabat, E. A. et al., 1991]. The V-region was located between amino acid No. 1 and No. 107 and $C_K$-region located from No. 108. And V-region also contained unique CDR 1,2,3 sequences, located between amino acid No. 24 and No. 34 (CDR 1), between No. 50 and No. 56 (CDR 2) and between No. 89 and No. 97 (CDR 3), which confer antigen-binding specificity. 5 Cysteins were found at amino acid numbers 23, 88, 134, 194 and 214, which would participate in disulfide bonding to form Fab structure of antibody.

As illustrated in Example 6 and Example 7, cDNAs encoding the heavy chain and light chain of the antigen-binding fragment (Fab) of monoclonal antibody MabB9 (IgG2b, kappa) against apolipoprotein B-100, the protein moiety of low-density lipoproteins(LDL) was shown to have all the requirements of antibody. Unique CDR sequences and some unusual amino acids were also found. These results strongly suggest that the cDNAs are functional.

The sequences were submitted to the GenBank/EMBL Data Libraries and have acquired the accession numbers of U28968 (heavy chain cDNA of MabB9; B9H) and U28969 (light chain cDNA of MabB9; B9L)(The sequences release date is Jan. 1, 1997).

<Example 8>

Nucleotide sequencing of heavy chain CDNA of murine monoclonal antibody MabB23 against human plasma apolipoprotein B-100.

To determine the nucleotide sequence of heavy chain cDNA, B23H in murine monoclonal antibody MabB23 against human plasma apoliporotein B-100, double stranded or single stranded phagemid DNA of pB23HT7 which contains the heavy chain cDNA (B23H) cloned in Example 5 was purified. Then, the same method as described in Example 6 was performed for nucleotide sequencing.

The determined nucleotide sequence of MabB23 heavy chain CDNA in MabB23 is shown in FIG. 7. When compared with the reported immunoglobulin heavy chain CDNA sequences, it was found that the heavy chain CDNA of MabB23, B23H, belongs to mouse heavy chain subgroup I(B) [(Kabat, E. A. et al., 1991]. The V-region was located between amino acid No. 1 and No. 119 and $C_H1$-region located from No. 120. And the V-region contained unique CDR 1,2,3 sequences, located between amino acid No. 31 and No. 35 (CDR 1), between No. 50 and No. 65 (CDR 2) and between No. 98 and No. 108 (CDR 3), which confer antigen-binding specificity. 7 Cysteins were found at amino acid numbers 22, 95, 134, 146, 201, 228 and 231, which would participate in disulfide bonding to form Fab structure of antibody.

When compared with V-region sequence profiles of mouse heavy chain subgroup I(B) [Harris, L. and Bajorath, 1995], some unusual amino acids were found at the following locations: Glu (No. 1), Val (No. 5) and Val (No. 96). A new amino acid in the heavy chain constant region, Arg (AGG) at amino acid No. 133 instead of Gly(GGG) was found, which has not been hitherto reported.

<Example 9>

Nucleotide sequencing of light chain cDNA of murine monoclonal antibody MabB23 against human plasma apolipoprotein B-100.

To determine the nucleotide sequence of light chain CDNA of the murine monoclonal antibody MabB23 against human plasma apoliporotein B-100, double stranded or single stranded phagemid DNA of pB23LBlue which contains light chain cDNA (B23L) cloned in Example 5 was purified. Then the same method as described in Example 6 was performed for nucleotide sequencing.

The determined nucleotide sequence of MabB23 light chain cDNA is shown in FIG. 8. When compared with the reported immunoglobulin light chain cDNA sequence, it was found that the light chain cDNA of MabB23, B23L belongs to a typical mouse lambda chain [Kabat, E. A. et al., 1991]. The V-region was located between amino acid No. 1 and No. 110 and $C_\lambda$-region located from No. 111. And the V-region contained unique CDR 1,2,3 sequences, located between amino acid No. 23 and No. 36 (CDR 1), between No. 52 and No. 58 (CDR 2), and between No. 91 and No. 99 (CDR 3), which confer antigen-binding specificity. 5 Cysteins were found at amino acid numbers 22, 90, 137, 196 and 214, which would participate in disulfide bonding to form Fab structure of antibody.

As illustrated in Example 8 and Example 9, cDNAs encoding the heavy chain and light chain of the antigen-binding fragment (Fab) of monoclonal antibody MabB23 (IgG2b, lambda) against apolipoprotein B-100, the protein moiety of low-density lipoproteins(LDL) were shown to have all the sequence requirements of antibody. Unique CDR sequences and some unusual amino acids were also found. These results strongly suggest that the CDNAs are functional.

The sequences were submitted to the GenBank/EMBL Data Libraries and have acquired the accession numbers of U28970 (heavy chain cDNA of MabB23; B23H) and U28967 (light chain cDNA of MabB23; B23L) (The sequences release date is Jan. 1, 1997). cDNAs of the present invention can be used for expression in microorganisms of the recombinant Fab antibodies specific for human plasma apolipoprotein B-100 of LDL. The recombinant antibodies can be utilized as a diagnostic agent to measure the concentration of plasma apolipoprotein B-100, a positive index for cardiovascular diseases and in global risk assessment of the disease. In addition, the recombinant antibodies can be used for development of an immunotherapeutic protein which can specifically bind with the harmful LDL-containing substances in blood for subsequent removal from circulation in relation to the development of arterosclerosis.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 690 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

| | | | | | |
|---|---|---|---|---|---|
| GAGGTGCAGC | TGGTGGAGTC | TGGAGCTGAG | CTGATGAAGC | CTGGGGCCTC | AGTGAAGATA | 60
| TCCTGCAAGG | CTACTGGCTA | CACATTCAGT | AGCTACTGGA | TAGAGTGGAT | AAAGCAGAGG | 120
| CCTGGACATG | GCCTTGAGTG | GACTGGAGAG | ATTTTACCTG | GAAGTGGTAC | TACTAAATAC | 180
| AATGAGAAGT | TCAAGGACAA | GGCCACATTC | ACTGCAGATA | CATCCTCCAA | CACAGCCTAC | 240
| ATGCAACTCA | GCAGCCTGAC | ATCTGAGGAC | TCTGCCGTCT | ATTACTGTGC | AAGATCGTAT | 300
| AGGTACGCCC | CTATGGACTA | CTGGGGTCAA | GGAACCTCAG | TCACCGTCTC | CTCAGCCAAA | 360
| ACAACACCCC | CATCAGTCTA | TCCACTGGCC | CCTGGGTGTG | GAGATACAAC | TGGTTCCTCC | 420
| GTGACTCTGG | GATGCCTGGT | CAAGGGCTAC | TTCCCTGAGT | CAGTGACTGT | GACTTGGAAC | 480
| TCTGGATCCC | TGTCCAGCAG | TGTGCACACC | TTCCCAGCTC | TCCTGCAGTC | TGGACTCTAC | 540
| ACTATGAGCA | GCTCAGTGAC | TGTCCCCTCC | AGCACCTGGC | CAAGTCAGAC | CGTCACCTGC | 600
| AGCGTTGCTC | ACCCAGCCAG | CAGCACCACG | GTGGACAAAA | AACTTGAGCC | CAGCGGGCCC | 660
| ATTTCAACAA | TCAACCCCTG | TCCTCCATGC | | | | 690

( 2 ) INFORMATION FOR SEQ ID NO:2:

( i ) SEQUENCE CHARACTERISTICS:
        ( A ) LENGTH: 642 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
| GATATCAAGA | TGACCCAGTC | TCCATCTTCC | ATGTATGCAT | CTCTAGGAGA | GAGAGTCACT | 60
| ATCACTTGCA | AGGCGAGTCA | GGACATTTAT | AGCTATTTAA | GCTGGTTCCA | GCAGAAACCA | 120
| GGGAAATCTC | CTAAGACCCT | GATCTATCGT | GCAAACAGAT | TGGTCGATGG | GGTCCCATCA | 180
| AGGTTCAGTG | GCAGTGGATC | TGGGCAAGAT | TATTCTCTCA | CCATCAGCAG | CCTGGAGTAT | 240
| GAAGATCTGG | GAATTTATTA | TTGTCTACAG | TTTGATGAGT | TTCCGTACAC | GTTCGGAGGG | 300
| GGGACCAAGC | TGGAAATAAA | ACGGGCTGAT | GCTGCACCAA | CTGTATCCAT | CTTCCCACCA | 360
| TCCAGTGAGC | AGTTAACATC | TGGAGGTGCC | TCAGTCGTGT | GCTTCTTGAA | CAACTTCTAC | 420
| CCCAAAGACA | TCAATGTCAA | GTGGAAGATT | GATGGCAGTG | AACGACAAAA | TGGCGTCCTG | 480
| AACAGTTGGA | CTGATCAGGA | CAGCAAAGAC | AGCACCTACA | GCATGAGCAG | CACCCTCACG | 540
| TTGACCAAGG | ACGAGTATGA | ACGACATAAC | AGCTATACCT | GTGAGGCCAC | TCACAAGACA | 600
| TCAACTTCAC | CCATTGTCAA | GAGCTTCAAC | AGGAATGAGT | GT | | 642

( 2 ) INFORMATION FOR SEQ ID NO:3:

( i ) SEQUENCE CHARACTERISTICS:
        ( A ) LENGTH: 693 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
| GAGGTGCAGC | TGGTGGAGTC | AGGACCTGGC | CTGGTGGCGC | CCTCACAGAG | CCTGTCCATC | 60
| ACGTGCACTG | TCTCAGGGTT | CTCATTAACC | GACTATGGTG | TAAGCTGGAT | TCGCCAGCCT | 120
| CCAGGAAAGG | GTCTGGAGTG | GCTGGGAGTA | ATTTGGGCTG | GTGGAAGCAC | ATTCTATAAT | 180

| | | | | | | |
|---|---|---|---|---|---|---|
| TCAGCTCTCA | AGTCCAGACT | GAGCATCAAC | AAGGACAACT | CCAAGAGCCA | AGTTTTCTTA | 240 |
| AAAATGAACA | GTCTGCACAC | TGATGACACA | GCCATGTACT | ACTGTGTCAA | ACATGAGGAT | 300 |
| AGGTACGACT | GGTACTTCGA | TGTCTGGGGC | GCAGGGACCA | CGGTCACCGT | CTCCTCAGCC | 360 |
| AAAACAACAC | CCCCATCAGT | CTATCCACTG | GCCCTAGGT | GTGGAGATAC | AACTGGTTCC | 420 |
| TCCGTGACTC | TGGGATGCCT | GGTCAAGGGC | TACTTCCCTG | AGTCAGTGAC | TGTGACTTGG | 480 |
| AACTCTGGAT | CCCTGTCCAG | CAGTGTGCAC | ACCTTCCCAG | CTCTCCTGCA | GTCTGGACTC | 540 |
| TACACTATGA | GCAGCTCAGT | GACTGTCCCC | TCCAGCACCT | GGCCAAGTCA | GACCGTCACC | 600 |
| TGCAGCGTTG | CTCACCCAGC | CAGCAGCACC | ACGGTGGACA | AAAAACTTGA | GCCCAGCGGG | 660 |
| CCCATTTCAA | CAATCAACCC | CTGTCCTCCA | TGC | | | 693 |

( 2 ) INFORMATION FOR SEQ ID NO:4:

( i ) SEQUENCE CHARACTERISTICS:
        ( A ) LENGTH: 642 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

| | | | | | | |
|---|---|---|---|---|---|---|
| CAGGCTGTTG | TGACTCAGGA | ATCTGCACTC | ACCACATCAC | CTGGTGAAAC | AGTCACACTC | 60 |
| ACTTGTCGCT | CAAATACTGG | GGCAGTTACA | ACTAGTAACT | ATGCCAGCTG | GGTCCAAGAA | 120 |
| AAACCAGATC | ATTTATTCAC | TGGTCTAATA | GGTGGTACCA | ACAACCGAGT | TCCAGGTGTT | 180 |
| CCTGCCAGGT | TCTCAGGCTC | CCTGATTGGA | GACAAGGCTG | CCCTCACCAT | CACAGGGGCA | 240 |
| CAGACTGAGG | ATGAGGCAAT | ATATTTCTGT | GCTCTATGGA | ACAGCAACCA | CTGGGTGTTC | 300 |
| GGTGGAGGAA | CCAAACTGAC | TGTCCTAGGC | CAGCCCAAGT | CTTCGCCATC | AGTCACCCTG | 360 |
| TTTCCACCTT | CCTCTGAAGA | GCTCGAGACT | AACAAGGCCA | CACTGGTGTG | TACGATCACT | 420 |
| GATTTCTACC | CAGGTGTGGT | GACAGTGGAC | TGGAAGGTAG | ATGGTACCCC | TGTCACTCAG | 480 |
| GGTATGGAGA | CAACCCAGCC | TTCCAAACAG | AGCAACAACA | AGTACATGGC | TAGCAGCTAC | 540 |
| CTGACCCTGA | CAGCAAGAGC | ATGGGAAAGG | CATAGCAGTT | ACAGCTGCCA | GGTCACTCAT | 600 |
| GAAGGTCACA | CTGTGGAGAA | GAGTCTGTCT | CGTGCTGACT | GT | | 642 |

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:5:

Glu  Val  Gln  Leu  Val  Glu  Ser  Gly  Ala  Glu
    1                   5                            10

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: unknown ( i i ) MOLECULE TYPE: peptide (x i) SEQUENCE DESCRIPTION: SEQ ID NO:6:

Asp Ile Lys Met Thr Gln Ser Pro Ser Ser
1               5                   10

(2) INFORMATION FOR SEQ ID NO:7:

(i) SEQUENCE CHARACTERISTICS:
     (A) LENGTH: 10 amino acids
     (B) TYPE: amino acid
     (C) STRANDEDNESS: single
     (D) TOPOLOGY: unknown (ii) MOLECULE TYPE: peptide (x i) SEQUENCE DESCRIPTION: SEQ ID NO:7:

Glu Val Gln Leu Val Glu Ser Gly Pro Gly
1               5                   10

(2) INFORMATION FOR SEQ ID NO:8:

(i) SEQUENCE CHARACTERISTICS:
     (A) LENGTH: 10 amino acids
     (B) TYPE: amino acid
     (C) STRANDEDNESS: single
     (D) TOPOLOGY: unknown (ii) MOLECULE TYPE: peptide (x i) SEQUENCE DESCRIPTION: SEQ ID NO:8:

Gln Ala Val Val Thr Gln Glu Ser Ala Leu
1               5                   10

What is claimed is:

1. Vector pB23HT7, which contains cDNA (B23H) encoding the heavy chain of the murine antibody which binds human plasma apolipoprotein B-100.

2. Vector pB23LBlue, which contains cDNA (B23L) encoding the light chain of the murine antibody which binds human plasma apolipoprotein B-100.

3. Transformant TG1/pB23HT7 (accession number : KCTC 0199 BP), which is obtained by transforming *E. coli* with pB23HT7 of claim 1.

4. Transformant TG1/pB23LBlue (accession number : KCTC 0200 BP), which is obtained by transforming *E. coli* with pB23LBlue of claim 2.

5. A process for preparation, wherein TG1/pB23HT7 and TG1/pB23LBlue are cultured, vector pB23HT7 and vector pB23LBlue are purified and then, DNAs thereby obtained are used as starting materials for the production of recombinant antibodies which specifically bind human plasma apolipoprotein B-100.

6. cDNA which encodes an antigen-binding fragment (Fab) of a murine antibody which binds human plasma apolipoprotein B-100, said cDNA comprising:

a heavy chain (B23H) having the following nucleotide sequence SEQ. ID No. 3:

GAGGTGCAGC TGGTGGAGTC AGGACCTGGC

CTGGTGGCGC CCTCACAGAG CCTGTCCATC

ACGTGCACTG TCTCAGGGTT CTCATTAACC

-continued
GACTATGGTG TAAGCTGGAT TCGCCAGCCT

CCAGGAAAGG GTCTGGAGTG GCTGGGAGTA

ATTTGGGCTG GTGGAAGCAC ATTCTATAAT

TCAGCTCTCA AGTCCAGACT GAGCATCAAC

AAGGACAACT CCAAGAGCCA AGTTTTCTTA

AAAATGAACA GTCTGCACAC TGATGACACA

GCCATGTACT ACTGTGTCAA ACATGAGGAT

AGGTACGACT GGTACTTCGA TGTCTGGGGC

GCAGGGACCA CGGTCACCGT CTCCTCAGCC

AAAACAACAC CCCCATCAGT CTATCCACTG

GCCCCTAGGT GTGGAGATAC AACTGGTTCC

TCCGTGACTC TGGGATGCCT GGTCAAGGGC

TACTTCCCTG AGTCAGTGAC TGTGACTTGG

AACTCTGGAT CCCTGTCCAG CAGTGTGCAC

ACCTTCCCAG CTCTCCTGCA GTCTGGACTC

TACACTATGA GCAGCTCAGT GACTGTCCCC

TCCAGCACCT GGCCAAGTCA GACCGTCACC

TGCAGCGTTG CTCACCCAGC CAGCAGCACC

ACGGTGGACA AAAAACTTGA GCCCAGCGGG

CCCATTTCAA CAATCAACCC CTGTCCTCCA TGA;

and a light chain (B23L) having the following nucleotide sequence SEQ ID No. 4:

CAGGCTGTTG TGACTCAGGA ATCTGCACTC

ACCACATCAC CTGGTGAAAC AGTCACACTC

ACTTGTCGCT CAAATACTGG GGCAGTTACA

ACTAGTAACT ATGCCAGCTG GGTCCAAGAA

AAACCAGATC ATTTATTCAC TGGTCTAATA

GGTGGTACCA ACAACCGAGT TCCAGGTGTT

CCTGCCAGGT TCTCAGGCTC CCTGATTGGA

GACAAGGCTG CCCTCACCAT CACAGGGGCA

CAGACTGAGG ATGAGGCAAT ATATTTCTGT

GCTCTATGGA ACAGCAACCA CTGGGTGTTC

GGTGGAGGAA CCAAACTGAC TGTCCTAGGO

CAGCCCAAGT CTTCGCCATC AGTCACCCTG

TTTCCACCTT CCTCTGAAGA GCTCGAGACT

AACAAGGCCA CACTGGTGTG TACGATCACT

GATTTCTACC CAGGTGTGGT GACAGTGGAC

TGGAAGGTAG ATGGTACCCC TGTCACTCAG

GGTATGGAGA CAACCCAGCC TTCCAAACAG

AGCAACAACA AGTACATGGC TAGCAGCTAC

CTGACCCTGA CAGCAAGAGC ATGGAAAAGG

CATAGCAGTT ACAGCTGCCA GGTCACTCAT

GAAGGTCACA CTGTGGAGAA GAGTCTGTCT

CGTGCTGACT GT.

\* \* \* \* \*